United States Patent
Salazar-Ferrer et al.

(10) Patent No.: US 8,532,353 B2
(45) Date of Patent: Sep. 10, 2013

(54) SYNTHETIC VISUALIZATION AND QUANTIFICATION OF PERFUSION-RELATED TISSUE VIABILITY

(75) Inventors: Pascal Salazar-Ferrer, Eden Prairie, MN (US); Bennett W. Jackson, Minneapolis, MN (US); Stefan E. Atev, Minneapolis, MN (US)

(73) Assignee: Vital Images, Inc., Minnetonka, MN (US)

( * ) Notice: Subject to any disclaimer, the term of this patent is extended or adjusted under 35 U.S.C. 154(b) by 46 days.

(21) Appl. No.: 13/304,103

(22) Filed: Nov. 23, 2011

(65) Prior Publication Data

US 2013/0131507 A1    May 23, 2013

(51) Int. Cl.
*G06K 9/00* (2006.01)
*A61B 5/05* (2006.01)

(52) U.S. Cl.
USPC .............................. 382/128; 378/1; 600/407

(58) Field of Classification Search
None
See application file for complete search history.

(56) References Cited

U.S. PATENT DOCUMENTS

| | | | | |
|---|---|---|---|---|
| 5,269,315 A * | 12/1993 | Leuchter et al. | ............... | 600/544 |
| 5,961,454 A * | 10/1999 | Kooy et al. | .................... | 600/407 |
| 6,233,480 B1 | 5/2001 | Hochman et al. | | |
| 6,549,803 B1 * | 4/2003 | Raghavan et al. | ............ | 600/431 |
| 7,020,578 B2 | 3/2006 | Sorensen et al. | | |
| 7,512,435 B2 * | 3/2009 | Wu et al. | .......... | 600/431 |
| 7,580,737 B2 * | 8/2009 | Wintermark et al. | ......... | 600/407 |
| 7,627,078 B2 * | 12/2009 | Hsieh et al. | ....................... | 378/4 |
| 8,019,142 B2 * | 9/2011 | Nowinski et al. | ............. | 382/131 |
| 8,041,088 B2 * | 10/2011 | Mallya et al. | ................. | 382/128 |
| 8,090,164 B2 * | 1/2012 | Bullitt et al. | ................... | 382/128 |
| 8,121,375 B2 * | 2/2012 | Hu | ................ | 382/131 |
| 8,233,685 B2 * | 7/2012 | Chang et al. | ................. | 382/128 |
| 8,320,647 B2 * | 11/2012 | Djeridane | ..................... | 382/128 |
| 2002/0055092 A1 | 5/2002 | Hochman | | |
| 2004/0127799 A1 * | 7/2004 | Sorensen et al. | ............. | 600/481 |
| 2004/0210124 A1 * | 10/2004 | Nowinski et al. | ............. | 600/407 |
| 2004/0218794 A1 * | 11/2004 | Kao et al. | ....................... | 382/128 |
| 2005/0273001 A1 * | 12/2005 | Schmainda et al. | .......... | 600/411 |

(Continued)

FOREIGN PATENT DOCUMENTS

WO    WO2010005540 A4    1/2010

OTHER PUBLICATIONS

Bristow, Michael S. et al., "MR perfusion and diffusion in acute ischemic stoke: human gray and white matter have different thresholds for infarction", Journal of Cerebral Blood Flow & Metabolism (2005) 25, 1280-1287.

(Continued)

*Primary Examiner* — Manav Seth
(74) *Attorney, Agent, or Firm* — Faegre Baker Daniels LLP

(57) ABSTRACT

A computing system and method for generating, displaying and manipulating synthetic 2D and 3D brain tissue viability images and associated metrics from multiple perfusion maps derived from CT or other imaging system input image datasets. Stored linguistic tissue classification rules characterizing infarct, ischemic and/or normal or other tissue classes as a function of one or more perfusion parameters are used. The perfusion maps are normalized to normal brain tissue regions. Elements of the input image dataset are classified into one of the tissue classes as a function of the normalized perfusion maps and the classification rules. The classification includes ranking each of the plurality of tissue classes for elements of the input image dataset, and assigning one of the classes to elements of the dataset as a function of the ranks.

37 Claims, 9 Drawing Sheets

(56) References Cited

U.S. PATENT DOCUMENTS

| | | | |
|---|---|---|---|
| 2006/0142983 A1* | 6/2006 | Sorensen et al. | 703/11 |
| 2008/0021502 A1 | 1/2008 | Imielinska et al. | |
| 2008/0247622 A1* | 10/2008 | Aylward et al. | 382/131 |
| 2008/0319302 A1* | 12/2008 | Meyer et al. | 600/410 |
| 2009/0034812 A1* | 2/2009 | Nowinski et al. | 382/131 |
| 2009/0092308 A1* | 4/2009 | Deuerling-Zheng et al. | 382/132 |
| 2009/0129649 A1* | 5/2009 | Djeridane | 382/131 |
| 2010/0021035 A1 | 1/2010 | Gupta et al. | |
| 2010/0262017 A1 | 10/2010 | Frangioni | |
| 2011/0052024 A1 | 3/2011 | Nowinski | |
| 2011/0229003 A1 | 9/2011 | Yang | |

OTHER PUBLICATIONS

Eastwood, James D. et al., "Corelation of Early Dynamic CT Perfusion Imaging with Whole-Brain MR diffusion and Perfusion Imaging in Actute Hemispheric Stoke", AJNR Am J Neuroradio 24:1869-1875, Oct. 2003.

International Search Report and Written Opinion isued in PCT/US2012/066103 mailed Feb. 5, 2013.

Kudo, Kohsuke et al., "Differences in CT Perfusion Maps Generate by Different Commercial Software: Quantitative Analysis by Using Identical source Date of Acute Stroke Patients", Radiology, vol. 254: Number, pp. 200-209, Jan. 2010.

Lin, K. et al., "Accuracy of the Alberta Stroke Program Early CT Score during the First 3 Hours of Middle Cerebral Artery Stoke: Comparsion of Noncontrast CT, CT Angiography Source Image, and CT Perfusion", ANJR Am J Neuroradio 29:931-36, May 2008.

Pexman, J.J. Warwick et al., "Use of the Alberta Stroke Program Early CT Score (ASPECTS) for Assessing CT Scans in Patients with Acute Stroke", ANJR Am J Neuroradiol 22:1534-1542, Sep. 2001.

Ross, Timothy J., Fuzzy Logic With Engineering Applications, 2nd Edition, Copyright 2004 John Wiley & Sons Ltd. (entire book).

Schaefer, Pamela W. et al., "Predicting Cerebral Ischemic Infaret Volume with Diffusion and Perfusion MR Imaging", ANJR Am J Neuroradiol 23:1785-1794, Nov./Dec. 2002.

Sugene, M. et al., "Structure Identification of fuzzy model," Fuzzy Sets and Systems, vol. 26, No. 1, pp. 15-33, 1988.

Takagi, Tomohiro et al., "Fuzzy identification of systems and its application to modeling and control," IEEE Transactions on Systems, Man and Cybermetics, vol. 15, No. 1, pp. 116-132, Jan.-Feb. 1985.

* cited by examiner

SYNTHETIC VISUALIZATION AND QUANTIFICATION OF PERFUSION-RELATED TISSUE VIABILITY

TECHNICAL FIELD

The present invention relates generally to systems and methods for processing and displaying image data generated by medical imaging systems. In particular, the invention is a system and method for generating and displaying perfusion-related images representative of brain tissue viability.

BACKGROUND

Perfusion computed tomography (CT) imaging (PCT) of the brain is a commonly used modality for assessing damage to brain tissue following events such as strokes. PCT images or maps show the infarcted areas that may be irreversibly damaged and the ischemic area of tissue at risk that might be responsive to rehabilitative therapy (also referred to as the penumbra). Normally perfused tissue areas are also identified.

A number of different perfusion parameters can be determined from the image data produced by the imaging system and used to generate PCT images. These parameters include regional cerebral blood flow (rCBF), cerebral blood volume (CBV), mean transit time (MTT), perfusion weighted imaging (PWI), time-to-peak (TTP) and the delay. Commonly, a radiologist will assess the penumbra and infarcted tissue by reviewing 2D and/or 3D PCT images generated using one or more different perfusion parameters. The radiologist interprets these maps to identify the different brain tissue types. The results of these analyses are then used to select appropriate treatments. For example, an injury characterized by a relatively large infarct core and a comparatively small ischemic region may not be treated using reperfusion therapies. A relatively small infarct region surrounded by a large and salvageable ischemic area, on the other hand, may be a good candidate for these reperfusion therapies.

There remains, however, a continuing need for improved systems and methods for generating reliable perfusion-based tissue viability images. In particular, there is a need for systems and methods that can provide images accurately identifying the classes of the tissue. The ability to quickly provide images of these types would be especially desirable. Enhanced diagnoses and treatments leading to more effective patient outcomes may result.

SUMMARY

The invention is an improved system and method for generating PCT images. Synthetic images accurately categorizing brain tissue classes can be relatively quickly generated by the invention.

One embodiment of the invention is a method for operating a computing system to generate a brain tissue viability map from an input image dataset acquired from a patient's brain by a medical imaging system. For each of one or more different perfusion parameters, an imaged perfusion map of perfusion values is computed as a function of the input image dataset. A normal brain reference region is identified as a function of at least one of the one or more imaged perfusion maps. For each perfusion parameter, a normal perfusion value is identified as a function of perfusion values in the normal brain reference region. A normalized perfusion map is computed as a function of the imaged perfusion map and the normal perfusion value for each perfusion parameter. Linguistic tissue classification rules characterizing each of a plurality of tissue viability classes as a function of one or more of the one or more perfusion parameters are stored. Each element of the input image dataset is classified into one of the plurality of tissue viability classes as a function of the one or more normalized perfusion maps and the tissue classification rules. A brain tissue viability map is generated as a function of the classified elements of the input image dataset.

The one or more different perfusion parameters can be from a set of perfusion parameters including regional cerebral blood flow (rCBF), cerebral blood volume (CBV), mean transit time (MTT), time-to-peak (TTP), perfusion weighted imaging (PWI), permeability, absolute values of parametric perfusion maps. The plurality of tissue viability classes can be from classes including infarct tissue, ischemic tissue, oligemic tissue and normal perfused tissue.

In one embodiment of the invention, identifying the normal brain reference region includes comparing left side brain perfusion values to right side brain perfusion values of at least one of the one or more imaged perfusion maps to determine a side of the brain with a region of interest. A side of the brain contralateral to the side with the region of interest is identified as the normal brain reference region. Identifying a normal perfusion value includes computing a statistical representation of the perfusion values in the normal brain reference region in some embodiments.

In another embodiment of the invention classifying elements of the input image dataset includes ranking candidate classes for each voxel element of the input image dataset, and assigning one of the plurality of tissue classes to the voxel elements of the input dataset as a function of the ranks. A fuzzy classifier is used in one embodiment of the invention.

DETAILED DESCRIPTION

As described in detail below, the invention is a system and method for generating accurate synthetic brain tissue viability images (also referred to as maps) from a plurality of perfusion-related parameters such as regional cerebral blood flow (rCBF), cerebral blood volume (CBV), mean transit time (MTT), perfusion weighted imaging (PWI), time-to-peak (TTP), permeability, absolute values of parametric perfusion maps and the delay. This invention is particularly useful to radiologists and other clinicians in the context of ischemic stroke or other pathologies such as the cerebral vasospasm, and in most of the steno-occlusive diseases impacting the cerebral blood flow. The images can be relatively quickly generated, and enhance the ability of radiologists and clinicians to properly diagnose and treat these pathologies.

Figure 1:
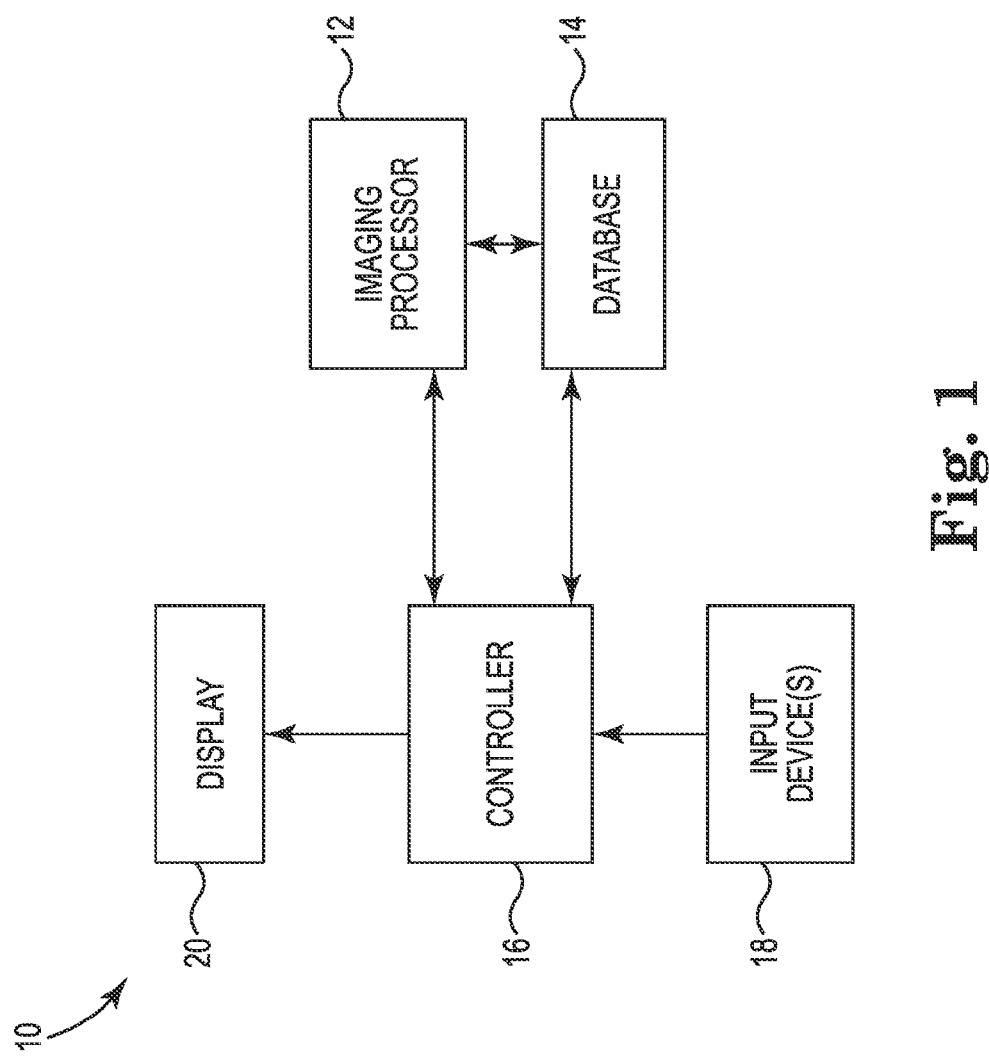
FIG. 1 is a block diagram of a computer system that can be used to generate and display synthetic tissue viability images and metrics in accordance with the invention.

FIG. 1 is a block diagram of a computer system 10 that can be used to generate and display synthetic tissue viability images in accordance with the present invention. As shown, system 10 includes an imaging processor 12 coupled to a database 14 and a controller 16. Controller 16 receives inputs from one or more input devices 18 and provides outputs to a display 20. The display 20, controller 16 and input devices 18 can be configured as a computer workstation with graphical user interface, and the input devices can include, for example, a mouse, keyboard touchpad or digital interactive pen. The controller 16 communicates with and controls both the imaging processor 12 and the database 14. In some embodiments the imaging processor 12 and the database 14 are located locally with the controller 16. In other embodiments the controller 16 communicates with and controls the imaging processor 12 and database 14 through a network such as the internet (e.g., through a web-based application run on the controller 16. Certain components of system 10 are illustrated in FIG. 1 in logical, functional form as opposed to structural, physical form. For example database 14 can be implemented as several, physically separate memory or data storage components, and can include conventional or otherwise known picture archiving and communication systems (PACS). Imaging processor 12 can also include associated data storage. Computer system 10 can be configured and programmed in any conventional or otherwise known manner suitable for performing the tissue viability imaging method described herein.

Figure 2:
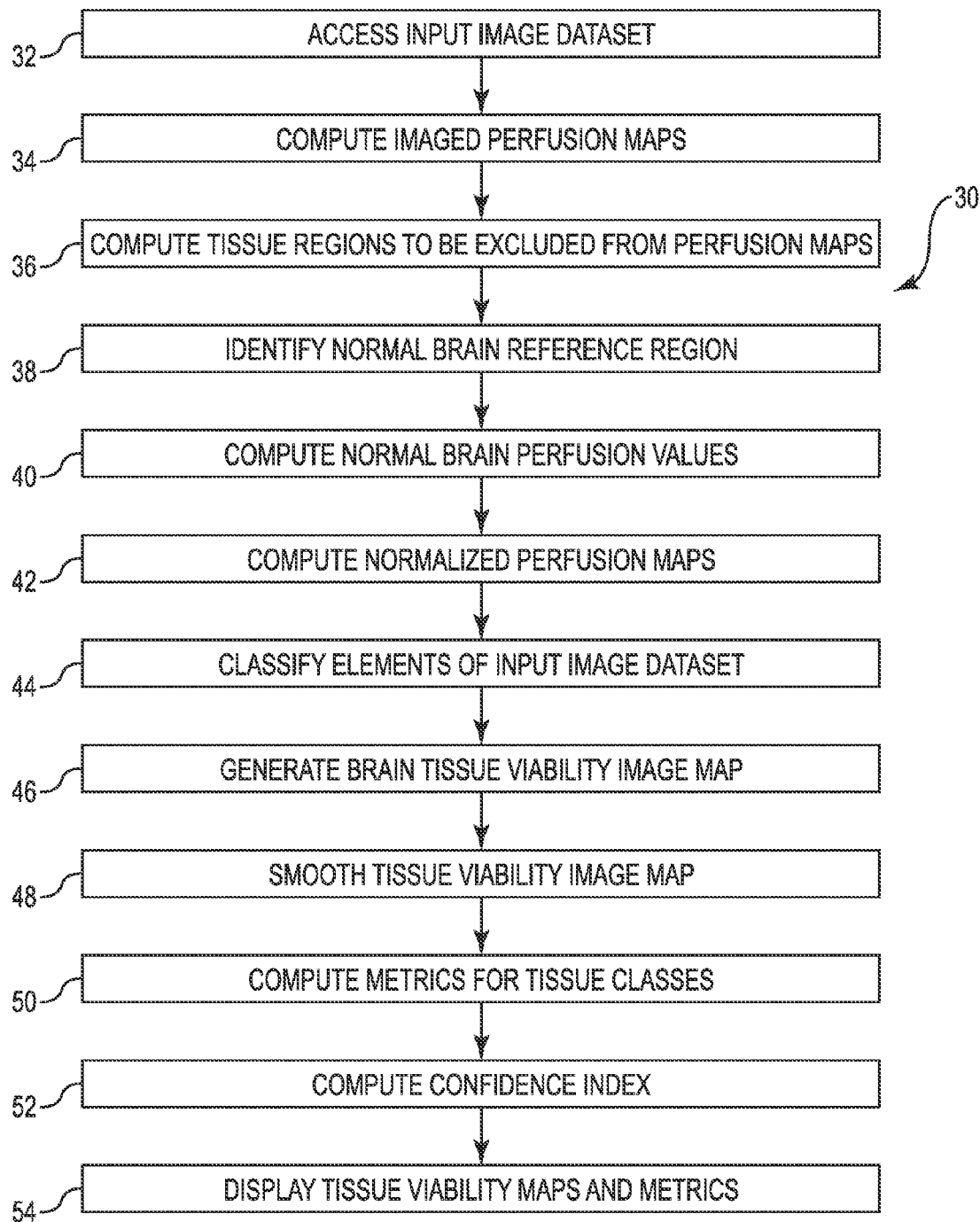
FIG. 2 is a high-level flowchart of the method for generating and displaying synthetic tissue viability images and metrics in accordance with the invention.

FIG. 2 is a flowchart describing one embodiment of the tissue viability visualization method 30 of the present invention. As noted above, method 30 can be performed using computer system 10. Viability visualization method 30 makes use of conventional input image datasets ($I_{Input\ Image}$) acquired by imaging a patient's brain using conventional medical imaging systems. The embodiment of the invention described herein uses computed tomography (CT) image data, although other embodiments use magnetic resonance (MR) or image data acquired using other imaging modalities. The input image datasets include sets of voxel data elements [$v_{II1}, v_{II2}, \ldots v_{IIN}$] representing a three-dimensional (3D) image of the brain volume. Each voxel data element represents the image value at a discrete location, or voxel, in the image volume. The input image datasets are typically organized as a series of adjacent two-dimensional (2D) arrays of voxel data elements, were each array represents a slice of the 3D volume.

As shown by step 32, an input image dataset associated with the patient is selected and accessed. One or more imaged perfusion maps (PI) are then computed from the input image dataset as shown by step 34. In one embodiment of the invention imaged perfusion maps for each of perfusion parameters rCBF ($PI_{CBF}$), CBV ($PI_{CBV}$), MTT ($PI_{MTT}$) and TTP ($PI_{TTP}$) are computed and used. In other embodiments of the invention, a greater or lesser number of imaged perfusion maps are used. Each imaged perfusion parameter map includes a set of perfusion value data elements ([$pi_{P1}, pi_{P2}, \ldots pi_{PN}$]) representative of the perfusion value of the brain tissue at the associated voxel. The imaged perfusion parameter maps represent perfusion images of the imaged brain. Conventional or otherwise known approaches can be used to compute the imaged perfusion maps. Information characterizing the perfusion mapping algorithms can be stored in memory. The MTT and CBV imaged perfusion datasets can, for example, be computed using different delay-sensitive or delay-insensitive algorithms. Perfusion maps are, for example, disclosed in the Kudo et al. article, Differences in CT Perfusion maps Generated by Different Commercial Software: "Quantitative Analysis by Using Identical Source Data of Acute Stroke Patients," *Radiology*, vol. 254, no. 1, January, 2010.

In some embodiments of the invention, certain regions of brain tissue are not used for further processing and are excluded from the imaged perfusion maps. In these embodiments of the invention the brain tissue regions to be excluded are computed as shown by step 36. By way of example, in one embodiment of the invention the voxel data elements associated with the ventricles and cerebrospinal fluid can be identified and excluded from further processing. Alternatively or in addition, the large blood vessels are identified and excluded from further processing in another embodiment of the invention.

Visualization method 30 makes use of relative or normalized perfusion maps for the perfusion parameters (e.g., $PN_{CBF}, PN_{CBV}, PN_{MTT}$, and $PN_{TTP}$ in one embodiment). In one embodiment of the invention the normalized perfusion maps are determined by identifying a normal brain reference region as shown by step 38, identifying normal perfusion values for each perfusion parameter as a function of the perfusion values in the normal brain region as shown by step 40, and computing the normalized perfusion maps as a function of the imaged perfusion datasets and the normal perfusion values as shown at step 42. The normal brain reference region is identified through the use of the TTP perfusion map in one embodiment of the invention because of the high degree of sensitivity of the TTP perfusion parameter to the presence of infarcted tissue in the lesion. In this embodiment, a group of perfusion value data elements of the TTP imaged perfusion map on one side of the brain (e.g., the left side brain voxels) are compared to a group of the perfusion value data elements for voxels at locations on the other side of the brain (e.g., the right side brain voxels). Conventional or otherwise known approaches can be used to identify brain symmetry and segment the left brain and right brain regions in connection with this reference region determination. Based on this comparison the side of the brain having the lesion (or other region of interest) is located. The side of the brain opposite or contralateral to the side with the lesion can then be identified as the normal brain reference region in accordance with step 38. The normal brain reference region will often roughly correspond to the middle cerebral artery (MCA) territory. The MCA territory may be the best candidate for the normal brain reference region because it is symmetric to the MCA territory with the lesion and most strokes affect the MCA territory on one side of the brain only. In situations where the imaged perfusion map shows a bilateral stroke involving other territories such as the posterior cerebral artery (PCA) or anterior cerebral artery (ACA) territories, the contralateral MCA territory can still offer a good normal reference. In other embodiments of the invention other or additional perfusion parameter maps can be processed to identify a normal brain reference region. Alternative approaches can be used to identify a normal brain reference region in other embodiments of the invention.

At step 42 a normal perfusion value is identified for each of the perfusion parameters (e.g., $VN_{CBF}$, $VN_{CBV}$, $VN_{MTT}$, $VN_{TTP}$ in one embodiment). In the embodiment of the invention described herein the normal perfusion values are values associated with voxels located in the normal brain reference region identified by step 38. The normal perfusion values can be statistical representations such as a mean (i.e., a central tendency) and standard deviation (i.e., a dispersion) of the values. These perfusion values can, for example, be computed using the frequency distribution of the perfusion values in the normal brain reference region. Other approaches, including but not limited to other statistical representations, can be used to characterize the normal perfusion values in other embodiments of the invention. For example, in other embodiments of the invention the dispersion of the distribution is not used as part of the normal perfusion values.

The normalized perfusion maps are computed as a function of the imaged perfusion maps and the normal perfusion values for each perfusion parameter. This computation step is shown generally at 42 in FIG. 2. The normalized perfusion values in the normalized perfusion maps represent the distance between the perfusion values of the corresponding voxels in the imaged perfusion datasets and the normal perfusion value. In the embodiment described above where the normal perfusion values are statistical representations, the normalized perfusion values can for example be representations of the distances from the mean values. The distances from the normal values can be expressed in terms of a percentage difference or in other (e.g., absolute distance, statistical distance) forms.

Each voxel data element of the input image dataset is classified into one of a plurality of tissue viability classes as a function of the normalized perfusion maps and a set of classification rules that characterize each of the tissue viability classes as a function of one or more perfusion parameters. This classification step is shown generally at 44 in FIG. 2. In one embodiment of the invention each voxel data element of the input image dataset is classified as being one of either infarct, ischemic or normal tissue. Other embodiments of the invention classify the voxel data elements into greater or lesser numbers of classifications (e.g., into classes including oligemic tissue). A fuzzy classification methodology (e.g., a 0-order classifier) is used for this purpose in one embodiment of the invention. In this embodiment of the invention the classification rules are stored in weighted, relative terms (e.g., in terms of distances of measured perfusion values from expected normal perfusion values so as to correspond to the distances represented by the values in the normalized perfusion maps). The rules can be stored in the terms of linguistic expressions of analysis and decision processes used by clinicians during usual, manual classification (e.g., "severely increased MTT," "normal MTT," and "reduced MTT). These rules can be expressed using continuous variables with progressive smooth transitions. Examples of these rules include (but are not limited to) the following:

1. An infarct region presents a reduced CBV associated with some increased or severely increased MTT and TTP.

2. An ischemic region presents a normal CBV and/or an increased CBV (because of auto-regulation following the ischemic event) together with increased MTT and TTP.

3. A normal region presents a normal CBV, a normal MTT and a normal TTP.

4. An ischemic region presents an increased CBV (because of auto-regulation following the ischemic event) or a normal CBV together with either an increased MTT or an increased CBF or an increased TTP.

The rules can be expressed in readable format (e.g., in .xml) and used as such by the classifier. The rules can then be easily updated based on the evolution of knowledge in stroke physiology, or on the application to other pathologies, patient conditions or acquisition. For example, the method can make use of new rules for the classification of brain tissue types such as oligemic penumbra (ischemic brain tissue able to recover without treatments) or the brain region susceptible to bleeding.

The normalized perfusion maps are processed in accordance with the rules to generate a rank for each tissue class in connection with each voxel data element of the input image dataset. In the embodiment of the invention described above, for example, each of the infarct, ischemic, and normal tissue classes will be assigned a rank (e.g., a numerical value between 0 and 1) for each voxel element. The voxels of the input image dataset are then classified as a function of the ranks. In one embodiment of the invention, the tissue type corresponding to the highest rank is assigned to the voxel element. For example, if for one voxel of the input image dataset the infarct rank was 0.1, the ischemic rank was 0.3 and the normal rank was 0.7, the voxel is classified as normal tissue.

Conventional or otherwise known fuzzy logic classifiers can be used for classification step 44. One embodiment of the invention, for example, uses known Takagi-Sugeno-Kang (TSK) classification methodologies to produce the weighted rule ranks. Other embodiments of the invention use other fuzzy logic classifiers or other rule-based classification approaches. By way of example, fuzzy logic classifiers of the types described in the following references, which are hereby incorporated by reference and for all purposes, can be used in the invention: T. Takagi et al., "Fuzzy identification of systems and its application to modeling and control," *IEEE Transactions on Systems, Man and Cybernetics*, vol. 15, no. 1, pp. 116-132, 1985; M. Sugeno et al., "Structure identification of fuzzy model," *Fuzzy Sets and Systems*, vol. 26, no. 1, pp. 15-33, 1988; T. Ross, Fuzzy Logic with Engineering Applications, $3^{rd}$ edition, Wiley, 2010.

After the voxels are classified, a brain tissue viability image map ($I_{Viability\ Image}$) can be generated as a function of the classifications as shown by step 46. The tissue viability image map is a set of voxel data elements $[v_{VT1}, v_{VT2}, \ldots v_{VTN}]$ representing the computed classification of the tissue corresponding to each voxel of the three-dimensional (3D) image of the brain volume. In the embodiment of the invention described above, each voxel data element is one of three values representing the infarct, ischemic and normal tissue classes.

As indicated by step 48, the tissue viability image map is optionally smoothened for purposes such as noise reduction and/or reducing local misclassifications at the voxel level. Conventional or otherwise known image smoothing algorithms can be implemented to perform the smoothing. One embodiment of the invention applies an iterative smoothing algorithm that reclassifies voxel data elements of the tissue viability image map as a function of the classification of voxels representative of adjacent tissue locations. For example, voxel data elements overwhelmingly surrounded by voxel data elements of a different class are reclassified into the class of the surrounding voxel elements.

Some embodiments of the invention generate quantitative analyses by computing metrics of the image represented by the tissue viability image map. This step is shown generally at 50 in FIG. 2. One embodiment of the invention, for example, computes the volume of tissue in each of the classes (e.g., infarct, ischemic and normal in one embodiment described above) in absolute terms (e.g., ml.) and/or as a percentage with respect to the total volume of brain tissue. Alternatively or in addition, the volume ratio of the infarct tissue to ischemic tissue (penumbra) can be computed.

Other embodiments of the invention optionally generate a confidence index that quantifies the accuracy of the classification as shown at step 52. The confidence index can be computed at the level of individual voxel data elements in the tissue viability image map, or at levels representative of larger areas of the image. A confidence index map at the individual voxel data element level in one embodiment of the invention is computed as a function of the differences between the assigned ranks of the voxels at classification step 30. For example, the confidence index value for a voxel can be high if the rank for the assigned classification (e.g., the best classification rank) is relatively high (e.g., close to the theoretical maximum) and is significantly greater than the next-best classification rank. If on the other hand the rank for the assigned classification is relatively low and/or is not significantly higher than the next-best classification rank, a lower confidence index value can be assigned to the voxel data element. A confidence index (CI) having a set of confidence index values ($[ci, ci_2, \ldots ci_N]$), each associated with one of the voxel elements in the tissue viability image map, can be computed in this manner. The confidence index values can be values within a continuous range, or alternatively values characterizing the confidence over a more limited range (e.g., "1" if acceptable confidence and "0" if low confidence). Other embodiments of the invention make use of more elaborate voxel-wise confidence index computation algorithms, such as those based on entropy measures.

Figure 3:
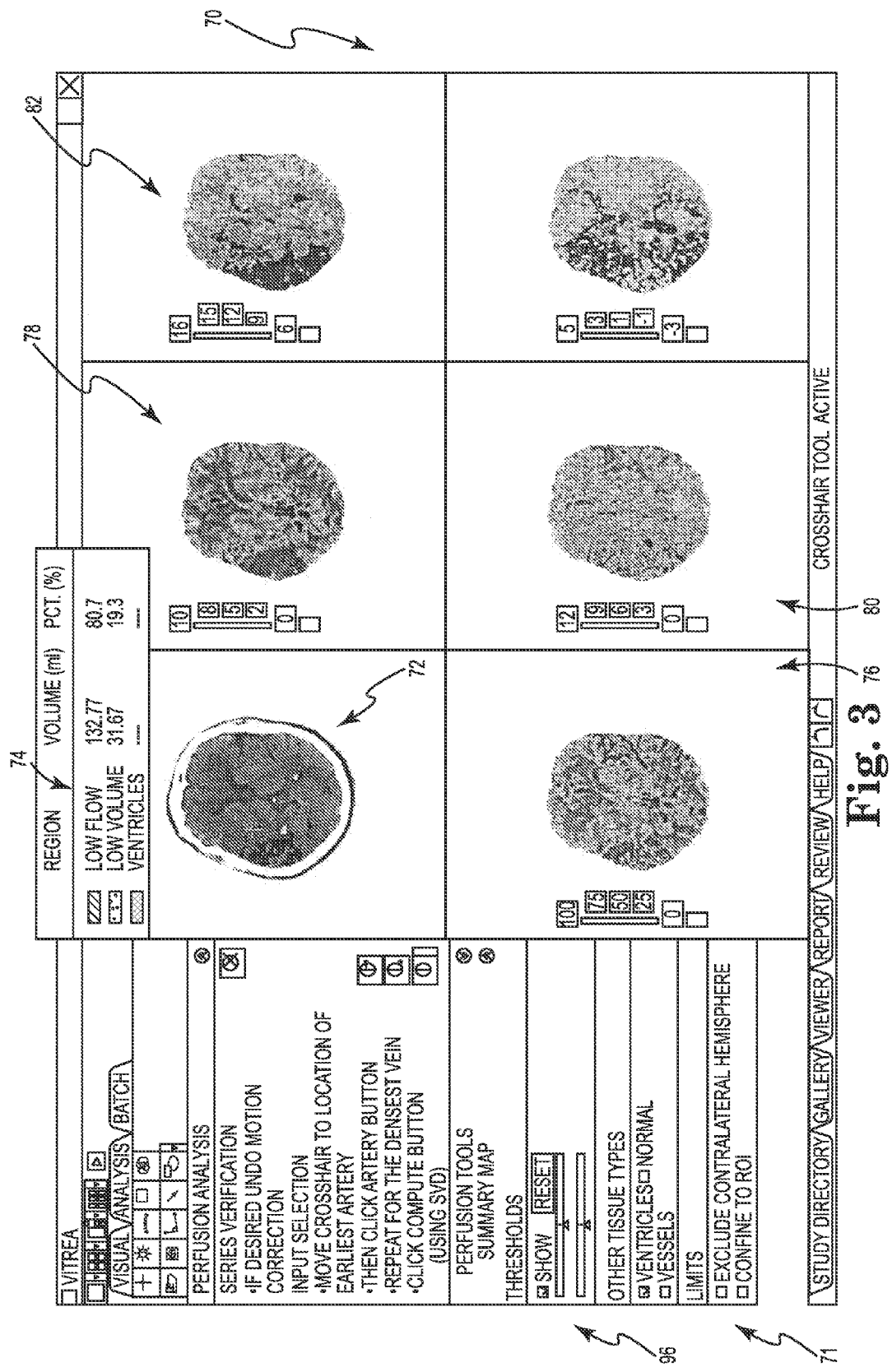
FIG. 3 is an illustration of a display including a graphical user interface, a synthetic tissue viability image, tissue viability metrics and several perfusion parameter maps generated in accordance with the method of the invention.

The image represented by the tissue viability image map and associated metrics such as the generated quantitative analyses and those represented by the confidence index can be displayed or visualized through a display and graphic user interface. This step is shown generally at 54 in FIG. 2. FIG. 3 is an illustration of a display 70 including a graphical user interface 71 and 2D tissue viability image 72, tissue viability metrics 74, 2D CBF image 76, 2D CBV image 78, 2D MTT image 80 and 2D TTP image 82 generated in accordance with method 30 above. Using tools on the interface 70 a clinician can display similar 2D and/or 3D images of different regions or slices of the imaged brain.

Figure 4:
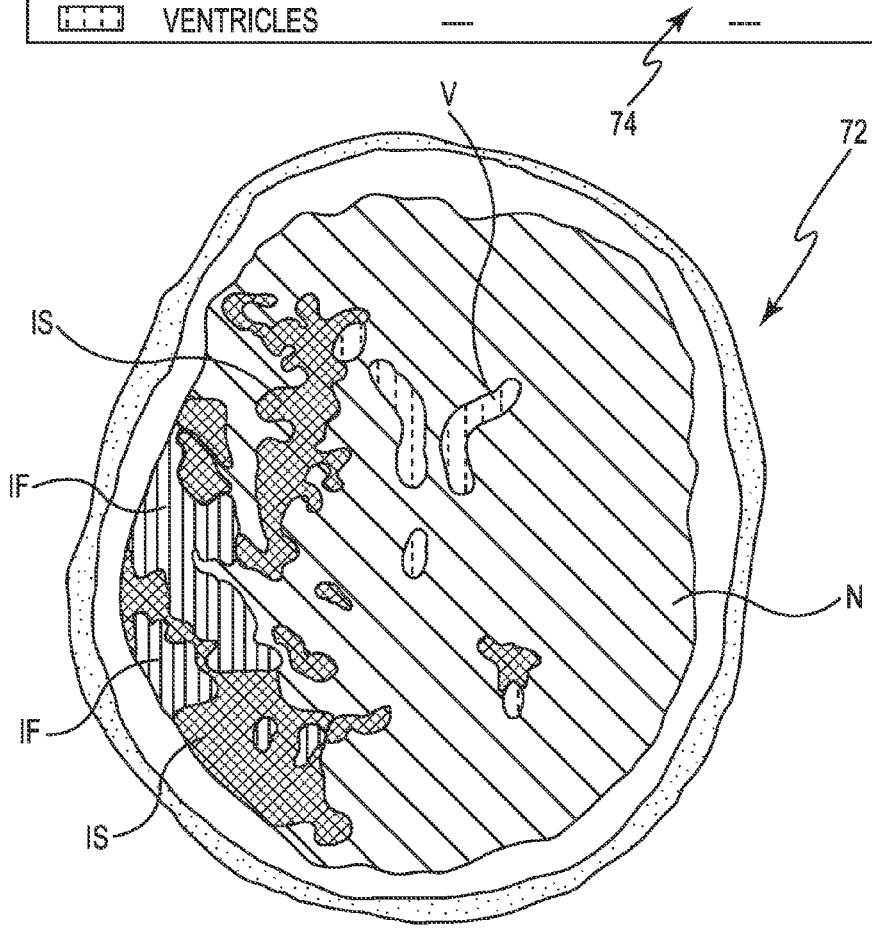
FIG. 4 is a detailed illustration of the tissue viability image and tissue viability metrics shown in FIG. 3.

FIG. 4 is detailed illustration of the portion of the display 70 including a synthetic brain tissue viability image 72 generated using data values from a tissue viability image map generated in accordance with the invention. In the image 72, infarct tissue IF is shown in red, ischemic tissue IS is shown in yellow, and normal tissue N is shown in gray. Image 72 also shows the ventricles V in violet. The displayed metrics 74 include the computed absolute and relative percentages of the volumes of the displayed infarct and ischemic regions, and is color keyed to the image 72. The displayed images of CBF image 76, CBC image 78, MTT image 80 and TTP image 82 in FIG. 3 can be of conventional other otherwise known form.

Figure 5:
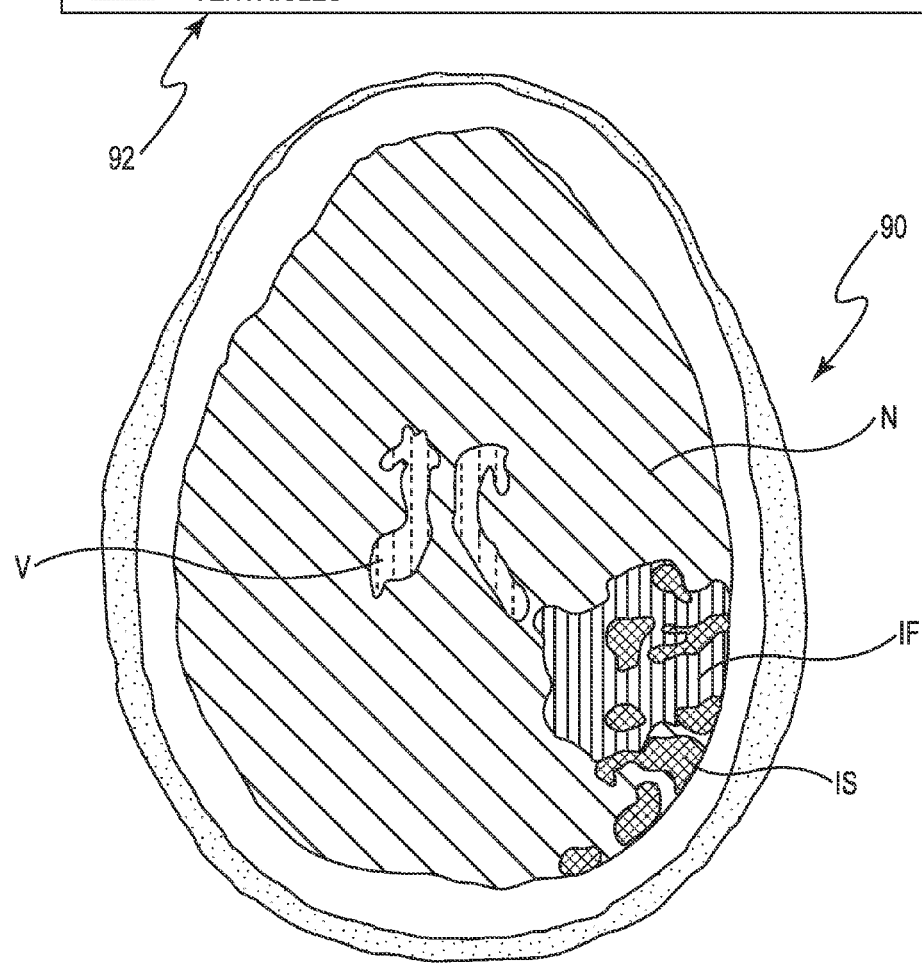
FIG. 5 is an illustration of another tissue viability image and tissue viability metrics generated in accordance with the method of the invention.

FIG. 5 is a detailed illustration of another tissue viability image 90 and associated metrics 92 generated using data from a tissue viability image dataset generated in accordance with the invention. In this image 90 the infarct tissue IF is shown in red, ischemic tissue IS is shown in yellow and normal tissue N is shown in green. The ventricles V are also shown in this image in violet. The displayed metrics 92 include the computed absolute and relative percentages of the volumes of the displayed infarct region IF, ischemic region IS and normal region N, and are color keyed to the image 90. Although not shown, synthetic color coded images similar to those described in connection with FIGS. 4 and 5 but in 3D volume rendered form can also be generated and displayed in a similar manner using the tissue viability image maps.

Figure 6A:
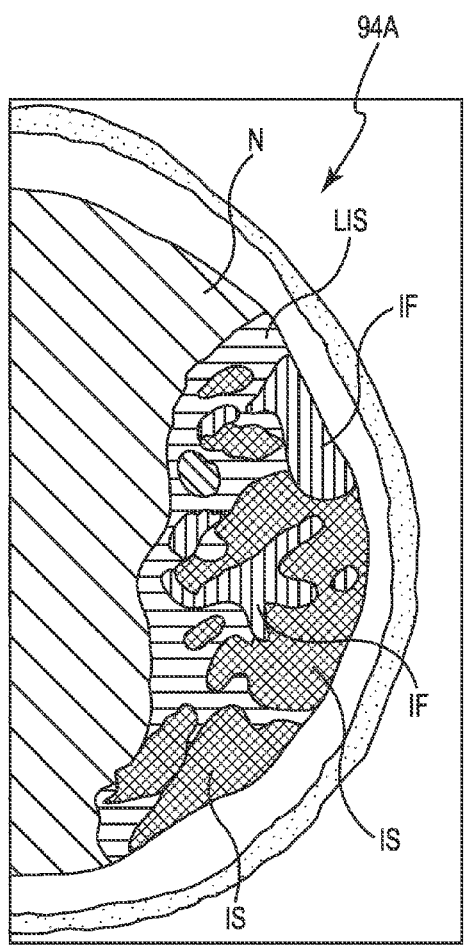
FIGS. 6A and 6B are illustrations of still other tissue viability images generated in accordance with the method of the invention. The images in both FIGS. 6A and 6B were generated from the same input image dataset and show the same brain region, but the image in FIG. 6B includes a visualization of a confidence index in accordance with one embodiment of the invention.
Figure 6B:
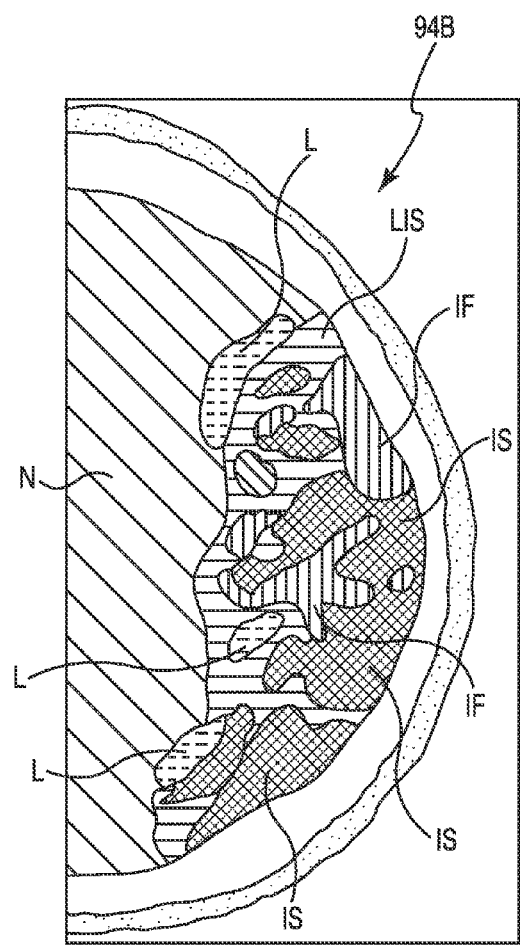

FIGS. 6A and 6B illustrate one approach for displaying and visualizing the information in the confidence index map. FIG. 6A is an illustration of a tissue viability image 94A with infarct tissue IF shown in red, regular ischemic tissue IS shown in yellow, low ischemic tissue LIS shown in blue, and normal tissue N shown in green. FIG. 6B is an illustration of a tissue viability image 94B generated from the same tissue viability image map used to generate image 94A, and of the same portion of the brain, but modified to reflect the associated confidence index map. In particular, portions L of the image characterized by the confidence index map as having a low confidence value are shown in gray in image 94B. In other embodiments of the invention an alternative visualization approach for displaying the confidence index applies a saturation scale for the colored map base on the confidence level values. In this alternative embodiment of the invention (not shown) the colored map is less saturated (more gray) for relatively low confidence value voxels, and more saturated (more vivid colors) for higher confidence value voxels.

Figure 7:
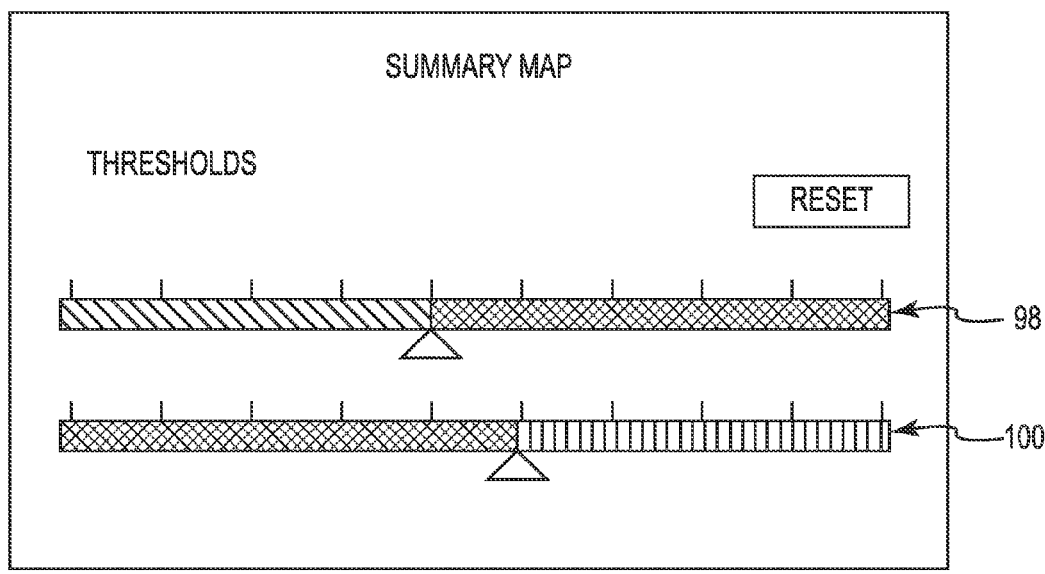
FIG. 7 a detailed illustration of the tuning control portion of the user interface shown in FIG. 3.

Graphical user interface 71 of the display 70 shown in FIG. 3 includes a fine tuning control 96 that can be actuated by a radiologist to adjust classification features such as sensitivity and specificity. Using the control 96 the radiologist can, for example, shift the relative weight of classification and the associated image display between different tissue classes. One embodiment of control 96 is shown in greater detail in FIG. 7. In this embodiment the control 96 includes slider bars 98 and 100, each of which controls the adjustment of different classification features. Slider bar 98 can be actuated by the radiologist to adjust the relative weight of classification between the normal class (shown in green on the left side of the bar) and the combined infarct and ischemic classes (i.e., the whole lesion) (shown in yellow on the right side of the bar). Slider bar 100 can be actuated by the radiologist to adjust the relative weight of classification between the infarct class (shown in yellow on the left side of the slider bar) and the ischemic region (shown in red on the right side of the slider bar).

The relative classification weighting is implemented during the generation of the tissue viability image map on the basis of the tuning level selected by the radiologist. If the one of slider bars 98 or 100 is moved after a viability image has been generated and displayed, the voxel data elements of the tissue viability image map corresponding to those in the displayed image are recalculated, and an updated viability image is generated using the recalculated viability image map. Alternatively, the entire viability image map is recalculated using the newly selected tuning levels. A radiologist can thereby dynamically change the display using the control 96.

In one embodiment of the invention the changes in classification weighting based on the controls 96 are done by grouping the perfusion parameters into different sets. Parameters in one set affect one relative classification of the tuning (e.g., the normal class versus the whole lesion for slider bar 98), and parameters in another set affect the other relative classification of the tuning (e.g., the infarct class versus the ischemic class for slider bar 100). A set of incrementally different (e.g., 10 increments for slider bars 98 and 100), weight values are established for each of the perfusion parameters (e.g., CBV, MTT, TTP) in the sets. These weight values are selected so that over the range of increments the ratio between the desired classifications vary between a desired minimum and a desired maximum. The lowest weight values will, for example, produce the minimum ratio between the classifications. The weight values corresponding to the selected tuning level are used during classification to allow a range of classifications (e.g., a more conservative or a more aggressive classification).

Figure 8A:
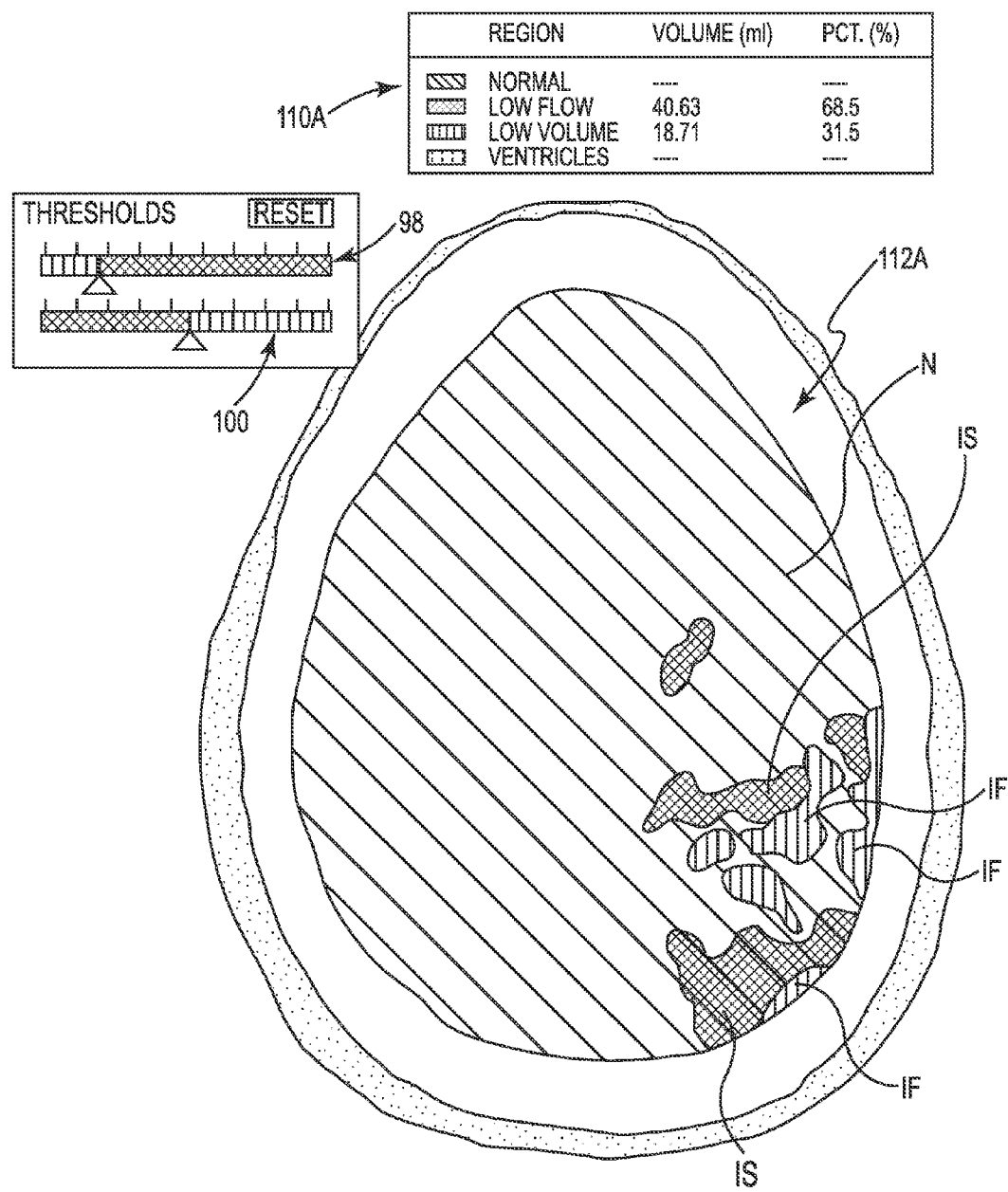
FIGS. 8A and 8B are illustrations of displays including a tissue viability image, tuning control and tissue viability metrics generated in accordance with the method of the invention. The images of both FIGS. 8A and 8B were generated from the same input image dataset and show the same brain region, but the images were generated with the infarct/ischemic region tuning control actuated to select different relative classification weights.
Figure 8B:
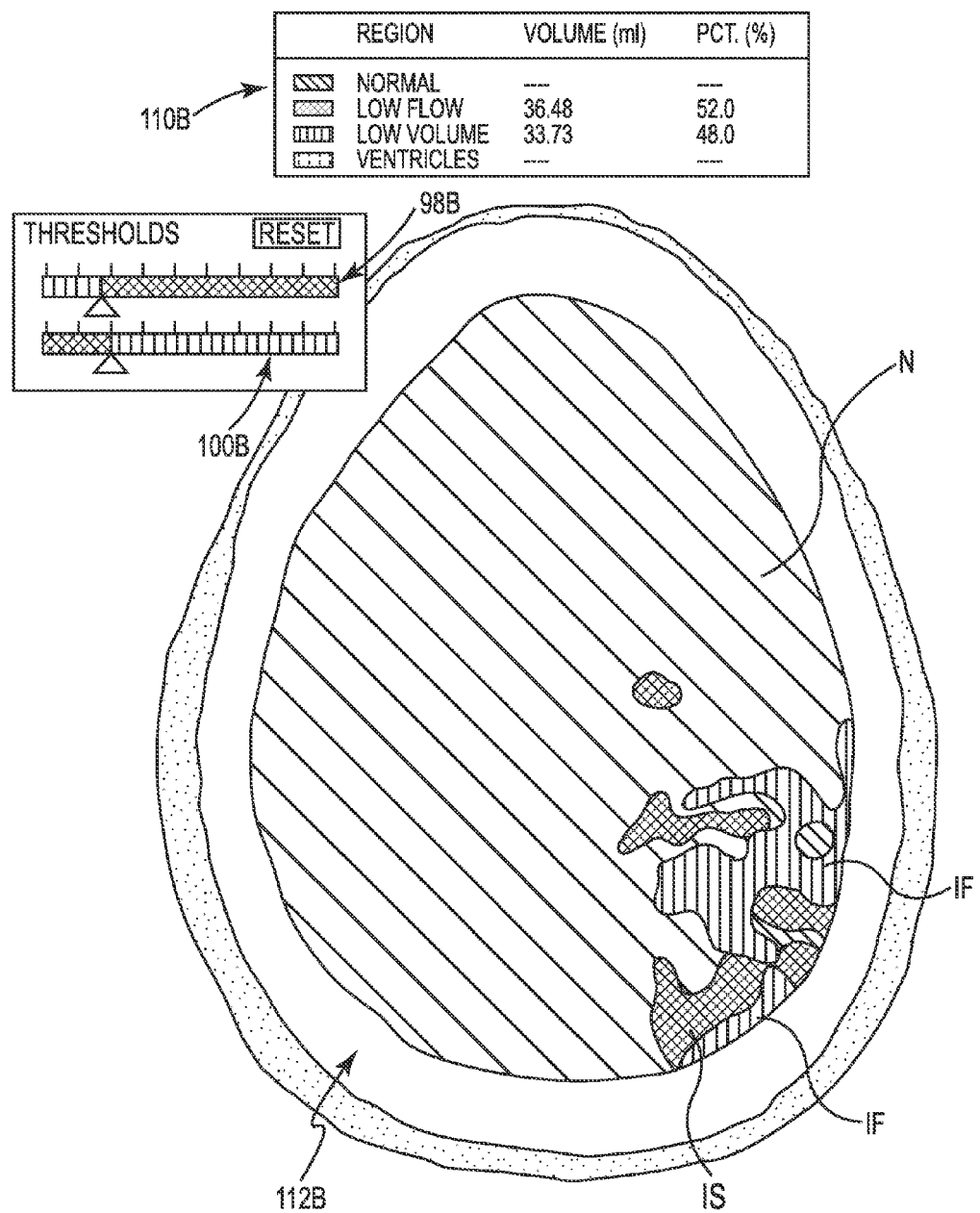

FIGS. 8A and 8B illustrate displays produced by the invention in response to actuation of the slider bar 100. The displays include tissue viability images 112A and 112B and associated slider bars 98A and 98B, 100A and 100B and metrics 110A and 110B. Images 112A and 112B were produced from tissue viability maps generated from the same input image dataset, and show the same brain region, but the images were generated with the infarct/ischemic region tuning control 100 actuated to select different relative classification weights. In images 112A and 112B infarct tissue IF is shown in red, ischemic tissue IS is shown in yellow, and normal tissue N is shown in green. Metrics 110A and 110B are color keyed to images 112A and 112B. As shown, infarct/ischemic slider bar 100B in FIG. 8B is actuated to more heavily weight the infarct class of tissue than slider bar 100A in FIG. 8A. Accordingly, more tissue in the image 112B has been classified as infarct tissue than in the image 112A. Metrics 110B also reflect the increased amount of infarct tissue in image 112B with respect to that in image 112A.

In some embodiments of the invention the input image dataset is processed to segment, or separately identify, different types of brain tissue represented by the dataset. For example, the cerebral ventricles, cerebrospinal fluid (CSF), white matter and gray matter can all be identified. Conventional or otherwise known medical image processing approaches can be used for this segmentation.

Other embodiments of the invention segment brain tissue between white matter and gray matter, and classify the tissue as a function of these different types of tissue. Conventional or otherwise known approaches can be used to segment the tissue represented by the input image dataset into either white matter or gray matter. Algorithms characterizing these approaches can be stored in memory. For example, the white matter versus gray matter segmentation can be based on a temporal average of a CT perfusion dataset. Computation of the imaged perfusion maps (step 34) can then be performed on selected tissue types to generate more accurate results. For example, the CBF perfusion parameter has a relatively high dependency on whether the parameter is being determined for white matter or gray matter. By using tissue type-specific imaged perfusion maps and associated normal brain perfusion values and classification rules (e.g., white matter-specific normalized perfusion maps, gray matter-specific normalized perfusion maps, and rules based on white matter-specific perfusion values and gray matter-specific perfusion values), increased signal to noise ratios can be achieved (e.g., tissue specific infarct and lesion classification can be achieved), thereby enhancing the accuracy of the tissue classification results.

The invention offers important advantages. It provides a robust tissue classification of brain tissues based on the perfusion properties of those tissues. This result is achieved because the invention is less sensitive to precise thresholds in perfusion parameters, and less sensitive to the variation among patients and among the radiological procedures. It can be used with no or minimal user adjustments. Rules can be conveniently and effectively stored and updated in a readable format comparable to the linguistic rules expressed in radiology. A number of aspects of the invention contribute to these results. They include: (1) the use of relative rules (as opposed to only rules involving absolute thresholds) with the automatic segmentation of a normal brain reference region, (2) the use of statistical distances to patient-based normal brain references instead of fixed predefined thresholds as an input to the classifier; (3) the integration of white matter/gray matter physiological differences in the classifier rules; (4) the parallel computational approach using a rule-based fuzzy classifier; (5) smoothing to reduce noise and local misclassification; and (6) the patient-specific approach.

In summary, the invention produces 2D and/or 3D viability maps that can be displayed as a colored overlay above CT images or in a 3D volume rendered region together with metrics such as the volumetric measurements for the different tissues. A user can easily and interactively fine tune the relative weights of the different tissue classes while watching the viability images resulting from the classification. Certain tissue such as the large cerebral vessels, cerebral spinal fluid and brain ventricles can be removed from the images and/or not used in the classification process. Local confidence of the classifications on a voxel level can be achieved and effectively visualized. The ability to classify tissue using rules specific to different types of tissue such as white matter and gray matter enhances classification accuracy. The classifications are largely insensitive to variability among patients, white/gray matter physiological differences, acquisition protocols and other clinical conditions. The rules are expressed in a flexible and readable format.

Although the present invention has been described in connection with certain embodiments, those skilled in the art will recognize that changes can be made in form and detail without departing from the spirit and scope of the invention. For example, although described in connection with an embodiment using particular CT perfusion techniques and rules, other perfusion parameters and/or other perfusion techniques such as magnetic resonance (MR) perfusion can also be used. Although described in connection with the diagnoses of lesions produced during strokes, the invention can be used in connection with other indications and/or other regions of interest. For example, the invention can be applied to cases of transient ischemic attacks, arteriovenous malformations, epilepsy and dementia (e.g., cerebral perfusion Acetazolamide imaging).

What is claimed is:

1. A method for operating a computing system to generate a brain tissue viability map from an input image dataset acquired from a patient's brain by a medical imaging system, comprising:

computing, for each of one or more different perfusion parameters, an imaged perfusion map of perfusion values as a function of the input image dataset;

identifying a normal brain reference region as a function of at least one of the one or more imaged perfusion maps;

identifying, for each perfusion parameter, a normal perfusion value as a function of perfusion values in the normal brain reference region;

computing, for each perfusion parameter, a normalized perfusion map as a function of the imaged perfusion map and the normal perfusion value;

storing linguistic tissue classification rules characterizing each of a plurality of tissue viability classes as a function of one or more of the one or more perfusion parameters;

classifying elements of the input image dataset into one of the plurality of tissue viability classes as a function of the one or more normalized perfusion maps and the tissue classification rules; and generating a brain tissue viability map as a function of the classified elements of the input image dataset.

2. The method of claim 1 wherein the one or more different perfusion parameters are from a set of perfusion parameters including regional cerebral blood flow (rCBF), cerebral blood volume (CBV), mean transit time (MTT), time-to-peak (TTP), perfusion weighted imaging (PWI) and permeability.

3. The method of claim 2 wherein the plurality of tissue viability classes are from a set classes including infarct tissue, ischemic tissue, oligemic tissue and normal perfused tissue.

4. The method of claim 1 wherein identifying the normal brain reference region includes:
comparing left side brain perfusion values to right side brain perfusion values of at least one of the one or more imaged perfusion maps to determine a side of the brain with a region of interest; and
identifying a side of the brain contralateral to the side with the region of interest as the normal brain reference region.

5. The method of claim 4 wherein identifying the normal brain reference region further includes identifying a middle cerebral artery (MCA) region.

6. The method of claim 5 wherein identifying the normal brain reference region includes identifying the normal brain reference region as a function of a perfusion map demonstrating a high sensitivity to abnormal brain tissue.

7. The method of claim 1 wherein identifying a normal perfusion value includes computing a statistical representation of the perfusion values in the normal brain reference region.

8. The method of claim 7 wherein computing a statistical representation includes computing a central tendency and optionally a dispersion of the perfusion values in the normal brain reference region.

9. The method of claim 8 wherein computing the central tendency and optionally a dispersion includes computing a mean and optionally a standard deviation of the perfusion values in the normal brain reference region.

10. The method of claim 7 wherein computing a normalized perfusion map includes computing a normalized perfusion map of elements representing statistical distances between elements of the imaged perfusion map and the normal perfusion value as a function of the statistical representation of the normal perfusion value.

11. The method of claim 7 wherein computing a normalized perfusion map includes computing a normalized perfusion map of elements representing distances between the elements of the imaged perfusion map and the normal perfusion value.

12. The method of claim 1 wherein:
storing tissue classification rules includes storing rules characterizing each of the tissue viability classes as a function of perfusion parameters; and
classifying elements of the input image data set includes:
ranking each of the plurality of tissue classes for voxel elements of the input image dataset; and
assigning one of the plurality of tissue classes to the voxel elements of the input dataset as a function of the ranks.

13. The method of claim 12 wherein storing tissue classification rules includes storing rules characterizing tissue viability classes as a function of relative values of perfusion parameters.

14. The method of claim 12 and further including computing a confidence index map representing a confidence value of elements of the brain tissue viability map as a function of the rankings.

15. The method of claim 14 and further including displaying a tissue viability image and confidence index as a function of the tissue viability map and the confidence index map.

16. The method of claim 1 and further including computing a confidence index map representing a confidence value of elements of the brain tissue viability map.

17. The method of claim 16 and further including displaying a tissue viability image and confidence index as a function of the tissue viability map and the confidence index map.

18. The method of claim 1 and further including smoothing the tissue viability map.

19. The method of claim 18 and further including displaying a tissue viability image as a function of the smoothened tissue viability map.

20. The method of claim 18 wherein smoothing the tissue viability map includes:
comparing classifications of adjacent elements of the tissue viability map; and
reclassifying elements of the tissue viability map as a function of the comparison.

21. The method of claim 1 wherein classifying elements of the input image dataset further includes tuning the classifications of the elements as a function of a user tuning input.

22. The method of claim 21 wherein classifying elements of the input image dataset includes weighting perfusion parameters as a function of the user tuning input.

23. The method of claim 21 wherein tuning the classifications of the elements includes tuning classifications between normal classifications and a group including infarct and ischemic classifications as a function of a user normal/abnormal weight control input.

24. The method of claim 21 wherein tuning the classifications of the elements includes tuning classifications between infarct classifications and ischemic classifications as a function of a user abnormal tissue core/penumbra weight control input.

25. The method of claim 21 and further including displaying a tissue viability image as a function of the tissue viability map representative of tuned classifications.

26. The method of claim 1 wherein:
storing tissue classification rules includes storing rules based on relative perfusion parameter values; and
classifying elements of the input image dataset includes fuzzy logic classifying the elements as a function of the one or more normalized perfusion maps and the tissue classification rules.

27. The method of claim 1 and further including displaying a tissue viability image as a function of the brain tissue viability map.

28. The method of claim 1 and further including pre-segmenting regions of interest from the one or more imaged perfusion maps, wherein the regions of interest are selected from a set including ventricles and vessels.

29. The method of claim 1 wherein:
identifying a normal perfusion value as a function of perfusion values in the normal brain reference region includes identifying perfusion values for white matter and gray matter;
computing a normalized perfusion map includes computing normalized perfusion maps for white matter and gray matter;

storing linguistic tissue classification rules includes storing white matter-specific rules and gray matter-specific rules; and classifying elements of the input image dataset includes classifying the elements as a function of the white matter and gray matter perfusion maps and the white matter-specific rules and gray matter-specific rules.

30. A method for operating a computing system to generate and display a brain tissue viability map from an input image dataset acquired from a patient's brain by a medical imaging system, comprising:

computing, for each of two or more different perfusion parameters, an imaged perfusion map of perfusion values as a function of the input image dataset;

identifying a normal brain reference region as a function of at least one of the imaged perfusion maps;

identifying, for each perfusion parameter, a normal perfusion value as a function of perfusion values in the normal brain reference region;

computing, for each perfusion parameter, a normalized perfusion map as a function of the imaged perfusion map and the normal perfusion value;

storing linguistic tissue classification rules characterizing each of a plurality of tissue viability classes as a function of one or more of the perfusion parameters;

classifying elements of the input image dataset into one of the plurality of tissue viability classes as a function of the normalized perfusion maps and the tissue classification rules; including:

ranking each of the plurality of tissue classes for elements of the input image dataset; and assigning one of the plurality of tissue classes to elements of the input image dataset as a function of the ranks;

generating a brain tissue viability map as a function of the classified elements of the input image dataset; and displaying a tissue viability image as a function of the brain tissue viability map.

31. The method of claim 30 and further including:
providing a user tuning control; and
tuning the classifications of the elements as a function of a user input from the user tuning control when classifying the elements.

32. The method of claim 31 and further including:
computing a confidence index representing a confidence value of elements of the tissue viability map as a function of the rankings; and
displaying a tissue viability image and confidence index as a function of the tissue viability map and the confidence index map.

33. The method of claim 32 wherein:
identifying a normal perfusion value as a function of perfusion values in the normal brain reference region includes identifying perfusion values for white matter and gray matter;
computing a normalized perfusion map includes computing normalized perfusion maps for white matter and gray matter;
storing linguistic tissue classification rules includes storing white matter-specific rules and gray matter-specific rules; and
classifying elements of the input image dataset includes classifying the elements as a function of the white matter and gray matter perfusion maps and the white matter-specific rules and gray matter-specific rules.

34. A computing system for generating and displaying a brain tissue viability map from an input image dataset acquired from a patient's brain by a medical imaging system, comprising:

a data store for storing information representative of:
a plurality of perfusion parameter mapping algorithms; and
linguistic tissue classification rules characterizing each of a plurality of tissue viability classes as a function of one or more perfusion parameters;

a processor coupled to the data store, wherein the processor:
computes, for each of two or more different perfusion parameters as a function of the perfusion parameter mapping algorithms, an imaged perfusion map of perfusion values as a function of the input image dataset;
identifies a normal brain reference region as a function of at least one of the imaged perfusion maps;
identifies, for each perfusion parameter, a normal perfusion value as a function of perfusion values in the normal brain reference region;
computes, for each perfusion parameter, a normalized perfusion map as a function of the imaged perfusion map and the normal perfusion value;
classifies elements of the input image dataset into one of the plurality of tissue viability classes as a function of the normalized perfusion maps and the tissue classification rules; including:
ranking each of the plurality of tissue classes for elements of the input image dataset; and
assigning one of the plurality of tissue classes to elements of the input image dataset as a function of the ranks; and
generates a brain tissue viability map as a function of the classified elements of the input image dataset; and a display to present a tissue viability image as a function of the brain tissue viability map.

35. The computing system of claim 34 wherein the processor:
causes a user tuning control to be presented on the display; and
tunes the classifications of the elements as a function of a user input from the user tuning control when classifying the elements.

36. The computing system of claim 35 wherein:
the processor computes a confidence index representing a confidence value of elements of the tissue viability map as a function of the rankings; and
the display presents a tissue viability image and confidence index as a function of the tissue viability map and the confidence index map.

37. The computing system of claim 36 wherein:
the data store stores tissue classification rules including white mater-specific rules and gray matter specific rules; and
the processor:
identifies normal perfusion values for white matter and gray matter;
computes normalized perfusion maps for white matter and gray matter; and
classifies elements as a function of the white matter perfusion maps and gray matter perfusion maps and the white matter-specific rules and gray matter-specific rules.

* * * * *